United States Patent [19]

Peterson

[11] 4,157,448

[45] Jun. 5, 1979

[54] ω-ARYL-12,13(E)-DIDEHYDRO-13,14-DIHYDRO-PGD COMPOUNDS

[75] Inventor: David C. Peterson, Portage, Mich.

[73] Assignee: The Upjohn Company, Kalamazoo, Mich.

[21] Appl. No.: 903,421

[22] Filed: May 8, 1978

Related U.S. Application Data

[62] Division of Ser. No. 809,248, Jun. 23, 1977, Pat. No. 4,099,014 and Ser. No. 809,249, Jun. 23, 1977, Pat. No. 4,142,052, which are a division of Ser. No. 614,244, Sep. 17, 1975.

[51] Int. Cl.² ........................................... C07C 177/00
[52] U.S. Cl. ..................................... 560/53; 560/51; 562/463; 562/461; 260/408; 260/410; 260/410.5; 260/413
[58] Field of Search ................... 560/53, 51; 562/463, 562/461; 260/408, 410, 410.5, 413

Primary Examiner—Paul J. Killos
Attorney, Agent, or Firm—Robert A. Armitage

[57] ABSTRACT

Prostaglandin analogs with the following cyclopentane ring structure:

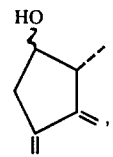

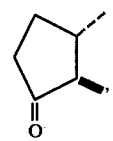

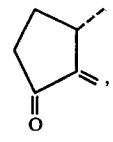

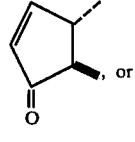

, or

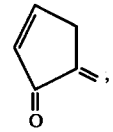

are disclosed along with intermediates useful in their preparation and processes for their preparation. These analogs are useful for some of the same pharmacological purposes as the prostaglandins, particularly and especially as blood platelet aggregation inhibitors.

127 Claims, No Drawings

ω-ARYL-12,13(E)-DIDEHYDRO-13,14-DIHYDRO-PGD COMPOUNDS

The present application is a divisional application of Ser. No. 809,249, filed June 23, 1977, now U.S. Pat. No. 4,142,052 issued Feb. 27, 1979; which is a divisional application of Ser. No. 614,244, filed Sept. 17, 1975, now pending. Likewise, U.S. Ser. No. 809,248, filed June 23, 1977, now U.S. Pat. No. 4,099,014 issued on July 4, 1978, is a divisional application of Ser. No. 614,244.

The present invention relates to prostaglandin analogs for which the essential material constituting a disclosure therefor is incorporated by reference here from U.S. Pat. No. 4,099,014.

I claim:

1. A prostaglandin analog of the formula

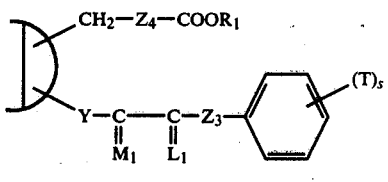

wherein

 is

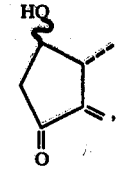

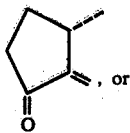, or

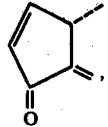

wherein Y is =CH—CH$_2$—;
wherein Z$_4$ is
 (1) cis-CH=CH—CH$_2$—(CH$_2$)$_g$—CF$_2$—,
 (2) cis-CH=CH—CH$_2$—(CH$_2$)$_g$—CH$_2$—,
 (3) cis-CH$_2$—CH=CH—(CH$_2$)$_g$—CH$_2$—,
 (4) —(CH$_2$)$_3$—(CH$_2$)$_g$—CF$_2$—, or
 (5) —(CH$_2$)$_3$—(CH$_2$)$_g$—CH2—,
wherein g is one, 2, or 3;
 wherein M$_1$ is

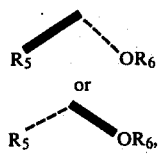

wherein R$_5$ and R$_6$ are hydrogen or methyl, with the proviso that one of R$_5$ and R$_6$ is methyl only when the other is hydrogen;
 wherein L$_1$ is

or a mixture of

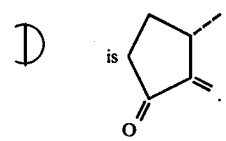

wherein R$_3$ and R$_4$ are hydrogen, methyl, or fluoro, being the same or different, with the proviso that one of R$_3$ and R$_4$ is hydrogen or fluoro only when the other is hydrogen or fluoro;
 wherein Z$_3$ is oxa or methylene
 wherein T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that Z$_3$ is oxa only when R$_3$ and R$_4$ are hydrogen or methyl, being the same or different; and
 wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A compound according to claim 1, wherein M$_1$ is

3. A compound according to claim 1, wherein M$_1$ is

4. A compound according to claim 3, wherein

D is

5. A compound according to claim 4, wherein Z$_3$ is methylene.

6. A compound according to claim 5, wherein s is zero or one and T is chloro, fluoro, or trifluoromethyl.

7. A compound according to claim 6, wherein Z$_4$ is cis-CH=CH—CH$_2$—(CH$_2$)$_g$—CF$_2$—, cis-CH=CH—CH$_2$—(CH$_2$)$_g$—CH$_2$—, or cis-CH$_2$—CH=CH—(CH$_2$)$_g$—CH$_2$—.

8. A compound according to claim 7, wherein g is one.

9. A compound according to claim 8, wherein $R_5$ and $R_6$ are both hydrogen.

10. A compound according to claim 9, wherein $R_3$ and $R_4$ are both hydrogen.

11. 2,2-Difluoro-17-phenyl-18,19,20-trinor-13,14-dihydro-12,13(E)-didehydro-9-deoxy-PGD$_2$, a compound according to claim 10.

12. 17-Phenyl-18,19,20-trinor-13,14-dihydro-12,13(E)-didehydro-9-deoxy-PGD$_2$, a compound according to claim 10.

13. cis-4,5-Didehydro-17-phenyl-18,19,20-trinor-13,14-dihydro-12,13(E)-didehydro-9-deoxy-PGD$_1$, a compound according to claim 10.

14. A compound according to claim 6, wherein $Z_4$ is —(CH$_2$)$_3$—(CH$_2$)$_g$—CF$_2$— or —(CH$_2$)$_3$—(CH$_2$)$_g$—CH$_2$—.

15. A compound according to claim 14, wherein g is one.

16. A compound according to claim 15, wherein $R_5$ and $R_6$ are both hydrogen.

17. A compound according to claim 15, wherein $R_3$ and $R_4$ are both hydrogen.

18. 2,2-Difluoro-17-phenyl-18,19,20-trinor-13,14-dihydro12,13(E)-didehydro-9-deoxy-PGD$_1$, a compound according to claim 17.

19. 17-Phenyl-18,19,20-trinor-13,14-dihydro-12,13(E)-didehydro-9-deoxy-PGD$_1$, a compound according to claim 17.

20. A compound according to claim 4, wherein $Z_3$ is oxa.

21. A compound according to claim 20, wherein s is zero or one and T is chloro, fluoro, or trifluoromethyl.

22. A compound according to claim 21, wherein $Z_4$ is cis-CH=CH—CH$_2$—(CH$_2$)$_g$—CF$_2$—, cis-CH=CH—CH$_2$—(CH$_2$)$_g$—CH$_2$—, or cis-CH$_2$—CH=CH—(CH$_2$)$_g$—CH$_2$—.

23. A compound according to claim 22, wherein g is one.

24. A compound according to claim 23, wherein $R_5$ and $R_6$ are both hydrogen.

25. A compound according to claim 24, wherein $R_3$ and $R_4$ are both hydrogen.

26. 2,2-Difluoro-16-phenoxy-17,18,19,20-tetranor-13,14-dihydro-12,13(E)-didehydro-9-deoxy-PGD$_2$, a compound according to claim 25.

27. 16-Phenoxy-17,18,19,20-tetranor-13,14-dihydro-12,13(E)-didehydro-9-deoxy-PGD$_2$, a compound according to claim 25.

28. cis-4,5-Didehydro-16-phenoxy-17,18,19,20-tetranor-13,14-dihydro-12,13(E)-didehydro-9-deoxy-PGD$_1$, a compound according to claim 25.

29. A compound according to claim 21, wherein $Z_4$ is —(CH$_2$)$_3$—(CH$_2$)$_g$—CF$_2$— or —(CH$_2$)$_3$—(CH$_2$)$_g$—CH$_2$—.

30. A compound according to claim 29, wherein g is one.

31. A compound according to claim 30, wherein $R_5$ and $R_6$ are both hydrogen.

32. A compound according to claim 31, wherein $R_3$ and $R_4$ are both hydrogen.

33. 16-Phenoxy-17,18,19,20-tetranor-13,14-dihydro-12,13(E)-didehydro-9-deoxy-PGD$_1$, a compound according to claim 32.

34. 2,2-Difluoro-16-phenoxy-17,18,19,20-tetranor-13,14-dihydro-12,13(E)-didehydro-9-deoxy-PGD$_1$, a compound according to claim 32.

35. A compound according to claim 3, wherein

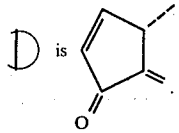

36. A compound according to claim 35, wherein $Z_3$ is methylene.

37. A compound according to claim 36, wherein s is zero or one and T is chloro, fluoro, or trifluoromethyl.

38. A compound according to claim 37, wherein $Z_4$ is cis-CH=CH—CH$_2$—(CH$_2$)$_g$—CF$_2$—, cis-CH=CH—CH$_2$—(CH$_2$)$_g$—CH$_2$—, or cis-CH$_2$—CH=CH—(CH$_2$)$_g$—CH$_2$—.

39. A compound according to claim 38, wherein g is one.

40. A compound according to claim 39, wherein $R_5$ and $R_6$ are both hydrogen.

41. A compound according to claim 40, wherein $R_3$ and $R_4$ are both hydrogen.

42. 2,2-Difluoro-17-phenyl-18,19,20-trinor-12,13(E)-didehydro-13,14-dihydro-9,10-didehydro-9-deoxy-PGD$_2$, a compound according to claim 41.

43. 17-Phenyl-18,19,20-trinor-12,13(E)-didehydro-13,14-dihydro-9,10-didehydro-9-deoxy-PGD$_2$, a compound according to claim 41.

44. 17-Phenyl-18,19,20-trinor-cis-4,5-Didehydro-12,13(E)-didehydro-13,14-dihydro-9,10-didehydro-9-deoxy-PGD$_1$, a compound according to claim 41.

45. A compound according to claim 37, wherein $Z_4$ is —(CH$_2$)$_3$—(CH$_2$)$_g$—CF$_2$— or —(CH$_2$)$_3$—(CH$_2$)$_g$—CH$_2$—.

46. A compound according to claim 45, wherein g is one.

47. A compound according to claim 46, wherein $R_5$ and $R_6$ are both hydrogen.

48. A compound according to claim 47, wherein $R_3$ and $R_4$ are both hydrogen.

49. 2,2-Difluoro-17-phenyl-18,19,20-trinor-12,13(E)-didehydro-13,14-dihydro-9,10-didehydro-9-deoxy-PGD$_1$, a compound according to claim 48.

50. 17-Phenyl-18,19,20-trinor-12,13(E)-didehydro-13,14-dihydro-9,10-didehydro-9-deoxy-PGD$_1$, a compound according to claim 48.

51. A compound according to claim 48, wherein $Z_3$ is oxa.

52. A compound according to claim 51, wherein s is zero or one and T is chloro, fluoro, or trifluoromethyl.

53. A compound according to claim 52, wherein $Z_4$ is cis-CH=CH—CH$_2$—(CH$_2$)$_g$—CF$_2$—, cis-CH=CH—CH$_2$—(CH$_2$)$_g$—CH$_2$—, or cis—CH$_2$—CH=CH—(CH$_2$)$_g$—CH$_2$—.

54. A compound according to claim 53, wherein g is one.

55. A compound according to claim 54, wherein $R_5$ and $R_6$ are both hydrogen.

56. A compound according to claim 55, wherein $R_3$ and $R_4$ are both hydrogen.

57. 2,2-Difluoro-16-phenoxy-17,18,19,20-tetranor-12,13(E)-didehydro-13,14-dihydro-9,10-didehydro-9-deoxy-PGD$_2$, a compound according to claim 56.

58. 16-Phenoxy-17,18,19,20-tetranor-12,13(E)-didehydro-13,14-dihydro-9,10-didehydro-9-deoxy-PGD$_2$, a compound according to claim 56.

59. cis-4,5-Didehydro-16-phenoxy-17,18,19,20-tetranor-12,13(E)-didehydro-13,14-dihydro-9,10-didehydro-9-deoxy-PGD$_1$, a compound according to claim 56.

60. A compound according to claim 52, wherein Z$_4$ is —(CH$_2$)$_3$—(CH$_2$)$_g$—CF$_2$— or —(CH$_2$)$_3$—(CH$_2$)$_g$—CH$_2$—.

61. A compound according to claim 60, wherein g is one.

62. A compound according to claim 61, wherein R$_5$ and R$_6$ are both hydrogen.

63. A compound according to claim 62, wherein R$_3$ and R$_4$ are both hydrogen.

64. 2,2-Difluoro-16-phenoxy-17,18,19,20-tetranor-12,13(E)-didehydro-13,14-dihydro-9,10-didehydro-9-deoxy-PGD$_1$, a compound according to claim 63.

65. 16-Phenoxy-17,18,19,20-tetranor-12,13(E)-didehydro-13,14-dihydro-9,10-didehydro-9-deoxy-PGD$_1$, a compound according to claim 63.

66. A compound according to claim 3, wherein

D is 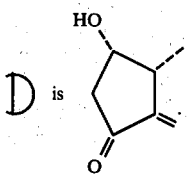

67. A compound according to claim 66, wherein Z$_3$ is methylene.

68. A compound according to claim 67, wherein s is zero or one and T is chloro, fluoro, or trifluoromethyl.

69. A compound according to claim 68, wherein Z$_4$ is cis-CH=CH—CH$_2$—(CH$_2$)$_g$—CF$_2$—, cis-CH=CH—CH$_2$—(CH$_2$)$_g$—CH$_2$—, or cis-CH$_2$—CH=CH—(CH$_2$)$_g$—CH$_2$—, 70. A compound according to claim 69, wherein g is one.

71. A compound according to claim 70, wherein R$_5$ and R$_6$ are both hydrogen.

72. A compound according to claim 71, wherein R$_3$ and R$_4$ are both hydrogen.

73. 2,2-Difluoro-17-phenyl-18,19,20-trinor-12,13(E)-didehydro-13,14-dihydro-9β-PGD$_2$, a compound according to claim 72.

74. 17-Phenyl-18,19,20-trinor-12,13(E)-didehydro-13,14-dihydro-9β-PGD$_2$, a compound according to claim 72.

75. cis-4,5-Didehydro-17-phenyl-18,19,20-trinor-12,13(E)-didehydro-13,14-dihydro-9β-PGD$_1$, a compound according to claim 72.

76. A compound according to claim 68, wherein Z$_4$ is —(CH$_2$)$_3$—(CH$_2$)$_g$—CF$_2$— or —(CH$_2$)$_3$—(CH$_2$)$_g$—CH$_2$—.

77. A compound according to claim 76, wherein g is one.

78. A compound according to claim 77, wherein R$_5$ and R$_6$ are both hydrogen.

79. A compound according to claim 77, wherein R$_3$ and R$_4$ are both hydrogen.

80. 2,2-Difluoro-17-phenyl-18,19,20-trinor-12,13(E)-didehydro-13,14-dihydro-9β-PGD$_1$, a compound according to claim 79.

81. 17-Phenyl-18,19,20-trinor-12,13(E)-didehydro-13,14-dihydro-9β-PGD$_1$, a compound according to claim 79.

82. A compound according to claim 66, wherein Z$_3$ is oxa.

83. A compound according to claim 82, wherein s is zero or one and T is chloro, fluoro, or trifluoromethyl.

84. A compound according to claim 83, wherein Z$_4$ is cis-CH=CH—CH$_2$—(CH$_2$)$_g$—CF$_2$—, cis-CH=CH—CH$_2$—(CH$_2$)$_g$—CH$_2$—, or cis-CH$_2$—CH=CH—(CH$_2$)$_g$—CH$_2$—.

85. A compound according to claim 84, wherein g is one.

86. A compound according to claim 85, wherein R$_5$ and R$_6$ are both hydrogen.

87. A compound according to claim 86, wherein R$_3$ and R$_4$ are both hydrogen.

88. 2,2-Difluoro-16-phenoxy-17,18,19,20-tetranor-12,13(E)-didehydro-13,14-dihydro-9β-PGD$_2$, a compound according to claim 87.

89. 16-Phenoxy-17,18,19,20-tetranor-12,13(E)-didehydro-13,14-dihydro-9β-PGD$_2$, a compound according to claim 87.

90. cis-4,5-Didehydro-16-phenoxy-17,18,19,20-tetranor-12,13(E)-didehydro-13,14-dihydro-9β-PGD$_1$, a compound according to claim 87.

91. A compound according to claim 83, wherein Z$_4$ is —(CH$_2$)$_3$—(CH$_2$)$_g$—CF$_2$— or —(CH$_2$)$_3$—(CH$_2$)$_g$—CH$_2$—.

92. A compound according to claim 91, wherein g is one.

93. A compound according to claim 92, wherein R$_5$ and R$_6$ are both hydrogen.

94. A compound according to claim 93, wherein R$_3$ and R$_4$ are both hydrogen.

95. 2,2-Difluoro-16-phenoxy-17,18,19,20-tetranor-12,13(E)-didehydro-13,14-dihydro-9β-PGD$_1$, a compound according to claim 94.

96. 16-Phenoxy-17,18,19,20-tetranor-12,13(E)-didehydro-13,14-dihydro-9β-PGD$_1$, a compound according to claim 94.

97. A compound according to claim 3, wherein

D is 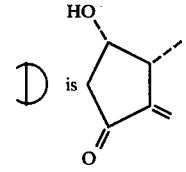

98. A compound according to claim 97, wherein Z$_3$ is methylene.

99. A compound according to claim 98, wherein s is zero or one and T is chloro, fluoro, or trifluoromethyl.

100. A compound according to claim 99, wherein Z$_4$ is cis-CH=CH—CH$_2$—(CH$_2$)$_g$—CF$_2$—, cis-CH=CH—CH$_2$—(CH$_2$)$_g$—CH$_2$—, or cis-CH$_2$—CH=CH—(CH$_2$)$_g$—CF$_2$—.

101. A compound according to claim 100, wherein g is one.

102. A compound according to claim 101, wherein R$_5$ and R$_6$ are both hydrogen.

103. A compound according to claim 102, wherein F$_3$ and R$_4$ are both hydrogen.

104. 2,2-Difluoro-17-phenyl-18,19,20-trinor-12,13(E)-didehydro-13,14-dihydro-PGD$_2$, a compound according to claim 103.

105. 17-Phenyl-18,19,20-trinor-12,13(E)-didehydro-13,14-dihydro-PGD$_2$, a compound according to claim 103.

106. cis-4,5-Didehydro-17-phenyl-18,19,20-trinor-12,13(E)-didehydro-13,14-dihydro-PGD$_2$, a compound according to claim 103.

107. A compound according to claim 99, wherein Z$_4$ is —(CH$_2$)$_3$—(CH$_2$)$_g$—CF$_2$— or —(CH$_2$)$_3$—(CH$_2$)$_g$—CH$_2$—.

108. A compound according to claim 107, wherein g is one.

109. A compound according to claim 108, wherein R$_5$ and R$_6$ are both hydrogen.

110. A compound according to claim 109, wherein R$_3$ and R$_4$ are both hydrogen.

111. 2,2-Difluoro-17-phenyl-18,19,20-trinor-12,13(E)-didehydro-13,14-dihydro-PGD$_1$, a compound according to claim 110.

112. 17-Phenyl-18,19,20-trinor-12,13(E)-didehydro-13,14-dihydro-PGD$_1$, a compound according to claim 110.

113. A compound according to claim 97, wherein Z$_3$ is oxa.

114. A compound according to claim 113, wherein s is zero or one and T is chloro, fluoro, or trifluoromethyl.

115. A compound according to claim 114, wherein Z$_4$ is cis-CH=CH—CH$_2$—(CH$_2$)$_g$—CF$_2$—, cis-CH=CH—CH$_2$—(CH$_2$)$_g$—CH$_2$—, or cis-CH$_2$—CH=CH—(CH$_2$)$_g$—CH$_2$—.

116. A compound according to claim 115, wherein g is one.

117. A compound according to claim 116, wherein R$_5$ and R$_6$ are both hydrogen.

118. A compound according to claim 117, wherein R$_3$ and R$_4$ are both hydrogen.

119. 2,2-Difluoro-16-phenoxy-17,18,19,20-tetranor-12,13(E)-didehydro-13,14-dihydro-PGD$_2$, a compound according to claim 118.

120. 16-Phenoxy-17,18,19,20-tetranor-12,13(E)-didehydro-13,14-dihydro-PGD$_2$, a compound according to claim 118.

121. cis-4,5-Didehydro-16-phenoxy-17,18,19,20-tetranor-12,13(E)-didehydro-13,14-dihydro-PGD$_1$, a compound according to claim 118.

122. A compound according to claim 114, wherein Z$_4$ is —(CH$_2$)$_3$—(CH$_2$)$_g$—CF$_2$—or —(CH$_2$)$_3$—(CH$_2$)$_g$—CH$_2$-.

123. A compound according to claim 122, wherein g is one.

124. A compound according to claim 123, wherein R$_5$ and R$_6$ are both hydrogen.

125. A compound according to claim 124, wherein R$_3$ and R$_4$ are both hydrogen.

126. 2,2-Difluoro-16-phenoxy-17,18,19,20-tetranor-12,13(E)-didehydro-13,14-dihydro-PGD$_1$, a compound according to claim 125.

127. 16-Phenoxy-17,18,19,20-tetranor-12,13(E)-didehydro-13,14-dihydro-PGD$_1$, a compound according to claim 125.

* * * * *

UNITED STATES PATENT OFFICE
CERTIFICATE OF CORRECTION

Patent No. 4,157,448   Dated 5 June 1979

Inventor(s) David C. Peterson

It is certified that error appears in the above-identified patent and that said Letters Patent are hereby corrected as shown below:

Patent should read as follows:

-- Related U.S. Application Data
[62] Division of Ser. No. 809,249, June. 23, 1977, Pat. No. 4,099,014, which is a division of Ser. No. 614,244, Sep. 17, 1975. --

Column 1, line 58, "(5) $-(CH_2)_3-(CH_2)_g-CH2-$" should read -- (5) $-(CH_2)_3-(CH_2)_g-CH_2-$ --.

Column 6, line 65, "$F_3$ and $R_4$" should read -- $R_3$ and $R_4$ --.

Signed and Sealed this

Twelfth Day of May 1981

[SEAL]

Attest:

RENE D. TEGTMEYER

Attesting Officer   Acting Commissioner of Patents and Trademarks